(12) United States Patent
Schmidt et al.

(10) Patent No.: US 7,004,320 B1
(45) Date of Patent: Feb. 28, 2006

(54) METHOD FOR PACKAGING OBJECTS AND A PACKAGING MATERIAL IN THE FORM OF A STRIP

(75) Inventors: Werner Schmidt, Forchheim (DE); Reinhard Kreuder, Forchheim (DE)

(73) Assignee: Huhtamaki Forchheim Zweigniederlassung der Huhtamaki Deutschland GmbH & Co. KG, Forchheim (DE)

( * ) Notice: Subject to any disclaimer, the term of this patent is extended or adjusted under 35 U.S.C. 154(b) by 103 days.

(21) Appl. No.: 10/129,347

(22) PCT Filed: Oct. 24, 2000

(86) PCT No.: PCT/EP00/10473

§ 371 (c)(1),
(2), (4) Date: Aug. 20, 2002

(87) PCT Pub. No.: WO01/32526

PCT Pub. Date: May 10, 2001

(30) Foreign Application Priority Data

Nov. 2, 1999 (DE) ................................ 199 52 569

(51) Int. Cl.
*A61B 17/06* (2006.01)
(52) U.S. Cl. ................. 206/441; 206/440; 604/385.02; 604/387
(58) Field of Classification Search ........ 206/438–441, 206/460, 813, 823; 602/54, 57–59; 604/386, 604/387, 358, 385.01–385.05
See application file for complete search history.

(56) References Cited

U.S. PATENT DOCUMENTS

| 4,264,008 | A | * | 4/1981 | Kozlow | 206/441 |
| 4,915,102 | A | * | 4/1990 | Kwiatek et al. | 206/440 |
| 5,333,753 | A | | 8/1994 | Etheredge | |
| 5,470,323 | A | * | 11/1995 | Smith et al. | 206/441 |
| 5,489,262 | A | * | 2/1996 | Cartmell et al. | 206/440 |
| 5,954,201 | A | * | 9/1999 | Finch et al. | 206/440 |
| 6,018,092 | A | * | 1/2000 | Dunshee | 206/440 |
| 6,036,679 | A | * | 3/2000 | Balzar et al. | 206/440 |
| 6,124,522 | A | * | 9/2000 | Schroeder | 206/440 |

FOREIGN PATENT DOCUMENTS

| DE | 35 41 753 | 5/1986 |
| GB | 2 298 627 | 9/1996 |
| WO | WO98 53781 | 12/1998 |
| WO | WO99 60965 | 12/1999 |

* cited by examiner

Primary Examiner—Luan K. Bui
(74) Attorney, Agent, or Firm—Collard & Roe, P.C.

(57) ABSTRACT

The invention relates to a method for packaging objects (4, 154, 164, 174, 184) which are at least partially self-adhesive by means of a packaging material (1, 30, 95, 151). Said packaging material segmentally comprises an anti-adhesive arrangement (2, 33, 93, 103, 124, 152, 162, 172, 175, 176, 182, 192), whereby the objects (4, 154, 164, 174, 184) are laid on the packing material with their self-adhesive section on the section of the packing material with an anti-adhesive arrangement (1, 30, 95, 151) and the objects (4, 154, 164, 174, 184) are finally covered by packing material (1, 30, 9, 151).

25 Claims, 8 Drawing Sheets

METHOD FOR PACKAGING OBJECTS AND A PACKAGING MATERIAL IN THE FORM OF A STRIP

Figure 1:
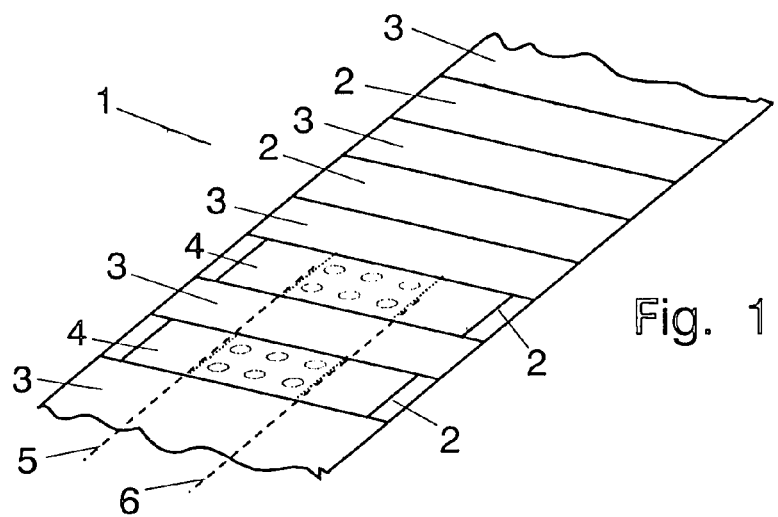

Applicants claim priority under 35 U.S.C. §119 of German Application No. 199 52 569.2 filed Nov. 2, 1999. Applicants also claim priority under 35 U.S.C. §365 of PCT/EP00/10473 filed Oct. 24, 2000. The international application under PCT article 21(2) was not published in English.

The invention relates to a process for the packaging of objects with a self-adhesive finish at least in places using a packaging material, sections of which are provided with a non-stick finish, whereby the objects are placed with their self-adhesive section on the sections of the packaging material that have been provided with a non-stick finish and the objects are then covered by packaging material.

In GB-A-2 298 627 a process for packaging similar objects is described.

A number of objects are conceivable that have a self-adhesive finish and need to have their adhesive surfaces protected during storage so that their adhesive properties are maintained. To make this possible, these surfaces are generally covered with a separate strip and then the complete object is packaged.

The purpose of the invention is to indicate a process with which both the self-adhesive finish can be protected and the entire object can be packaged in a simple way.

In the solution to this problem proposed by the invention, the objects are placed with their self-adhesive section on the sections of the packaging material that have been provided with a non-stick finish and the objects are then covered by packaging material.

In the solution to this problem proposed by the invention, a section of the packaging material is provided with the non-stick finish is used to cover the objects.

An advantageous further development of the invention is characterised by the fact that a section of the packaging material provided with the non-stick finish is used to cover the objects.

This makes it particularly easy to package the object, whereby either different or identical packaging materials can be used for both sides of the pack as a result.

It has also proved to be very advantageous if in accordance with the invention individual packs are divided off after the objects have been put into place.

In spite of the fact that they have been divided off, the individual packs can remain joined together and can be detached at a later time instead.

Division into individual packs is carried out in accordance with a further advantageous development of the invention by what is known as a crimping process.

In accordance with a further advantageous development of the invention, perforation lines are provided to facilitate the detachment of individual packs.

Particularly simple detachment of the individual packs is possible as a result.

A further advantageous development of the invention is characterised by the fact that the objects are packaged by wrapping them with at least one of the two edge strips.

A largely closed pack is produced in this way that provides the objects with sufficient protection.

It is very advantageous if in accordance with a further advantageous development of the invention at least one free flap is provided at the edge of the pack.

The pack is made easy to open as a result.

In a further advantageous development of the process proposed by the present invention, sticking-plasters provided with two adhesive sections are packaged, where the sections with a non-stick finish are provided at least in the area of the adhesive sections.

A further advantageous development of the process proposed by the present invention is characterised by the fact that panty liners are packaged that are provided with at least one self-adhesive section, in the area of which a section with a non-stick finish is provided.

A development of the invention is also very advantageous according to which sanitary towels are packaged that are provided with at least one self-adhesive section, in the area of which a section with a non-stick finish is provided.

In a further advantageous development of the process proposed by the present invention, the outside of the wrapper has a textile look and the non-stick finish on the inside of the wrapper is provided in sections.

It is very advantageous in this context if in accordance with a further development of the invention the wrapper is formed by a plastic film, the outside of which is embossed to give it a textile look.

It is also advantageous in this context if the wrapper is formed by a plastic film that is embossed on the outside and is smooth on the inside.

In a further advantageous development of the invention, the wrapper contains a nonwoven fabric.

It has also proved to be very advantageous if in accordance with a further development of the invention the nonwoven fabric is bonded to a plastic film, preferably on its inside.

All these different developments help to provide the wrapper with a comfortable outer surface that can be designed to meet the tightness requirements in each individual case.

A further advantageous development of the invention in connection with a web-like packaging material for the wrapping on at least approximately all sides of an object that is to be packaged and that is provided with an adhesive on at least sections of one side is characterised by the fact that the section of the packaging material which faces the adhesive is provided with non-stick sections, next to which sections are provided that do not have any non-stick material applied to them.

It is possible as a result to package objects that are adhesive on one side with the wrapper so that they are easy to remove again. It is, however, also possible to seal or crimp the sections that are not provided with the coating together to form the wrapper.

In a further advantageous development of the invention, at least one edge strip of the web of packaging material does not have any non-stick material applied to it.

Simple closure of the pack at its edges is guaranteed in this way.

According to a further development of the invention, it is very advantageous if an uninterrupted or interrupted longitudinal strip with a non-stick finish is provided in the middle of the web of packaging material, while at least the two longitudinal edges do not have a non-stick finish.

It has also proved to be very advantageous if in accordance with a further development of the invention several longitudinal strips with a non-stick finish and longitudinal strips without a non-stick finish alternate parallel to each other.

It is in addition very advantageous if in accordance with a further development of the invention individual sections with a non-stick finish are provided that are located in accordance with the objects that are to be packaged and their adhesive coating.

It has also proved to be very favourable if in accordance with a further development of the invention the non-stick finish consists of polysiloxanes that are cured.

A further advantageous development of the invention is characterised by the fact that the web of packaging material consists of a plastic film in the form of a monofilm or a multilayer film that can be embossed.

In accordance with a further development of the invention, the web of packaging material can, however, consist of paper too, which is preferably coated with plastic on at least one side.

A further development of the present invention is characterised by the fact that the web of packaging material consists of a nonwoven fabric that is preferably provided on one side with plastic.

In a further advantageous development of the invention, a longitudinal section of the web of packaging material is provided as a wrapper to package an object that has an adhesive finish on one side.

It is also very advantageous if in accordance with a further development of the invention the location of the non-stick finish is chosen according to the object that is to be packaged.

In a further advantageous development of the invention involving a web-like packaging material for packaging a sanitary towel, the sanitary towel is provided with side wings, in the area of which the non-stick finish is provided.

It is also very advantageous if in accordance with a further development of the invention the side of the web of packaging material facing away from the non-stick finish is provided with a print motif.

Figure 2:
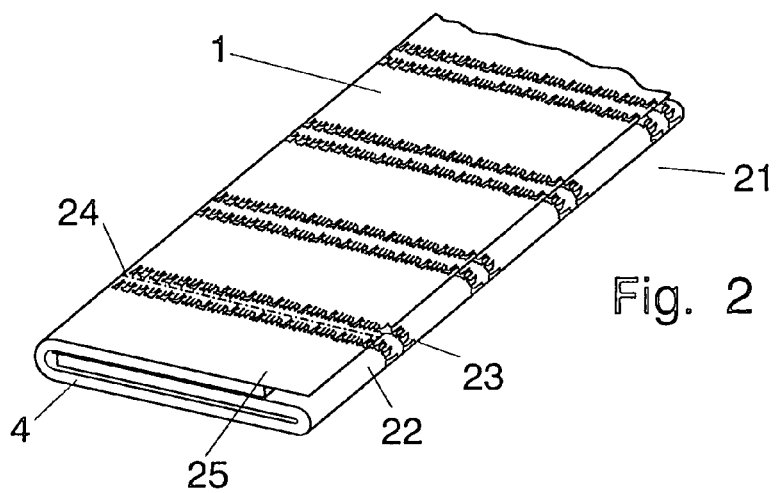
Figure 3:
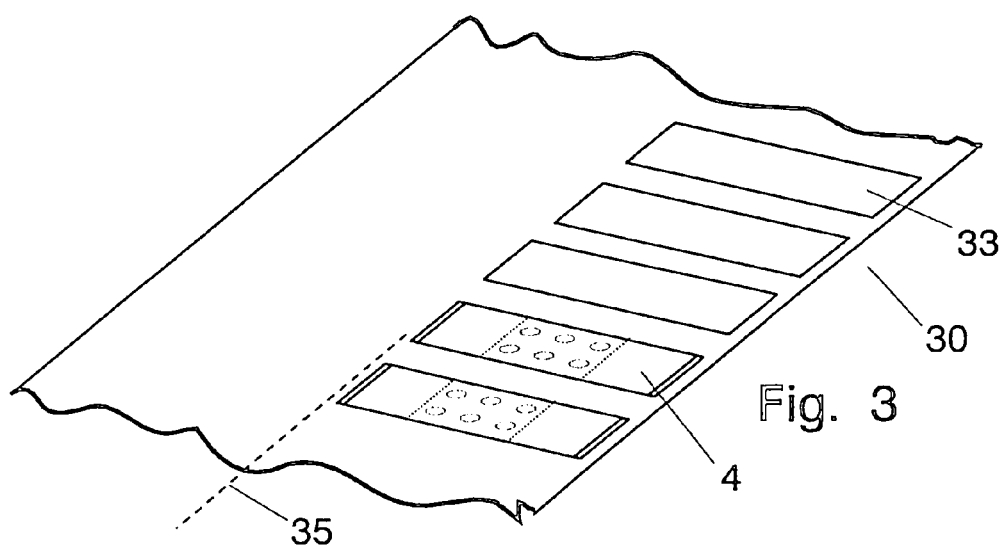
Figure 4:
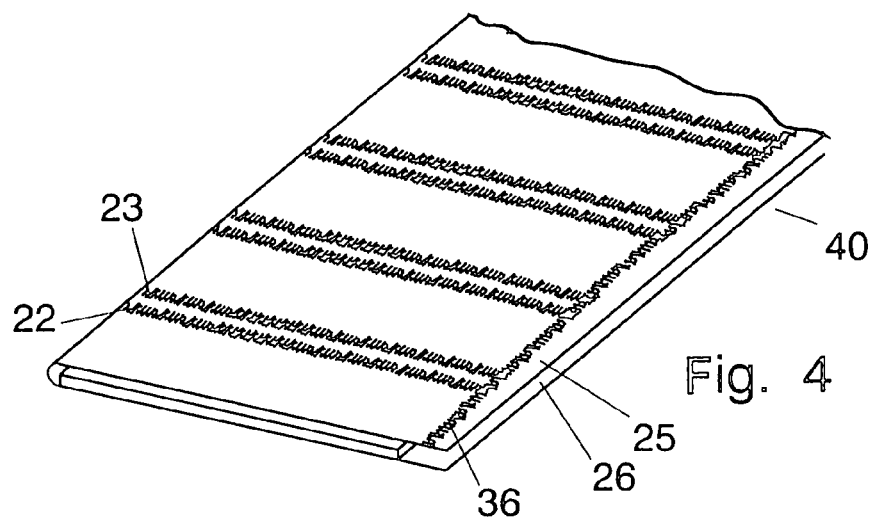
Figure 5:
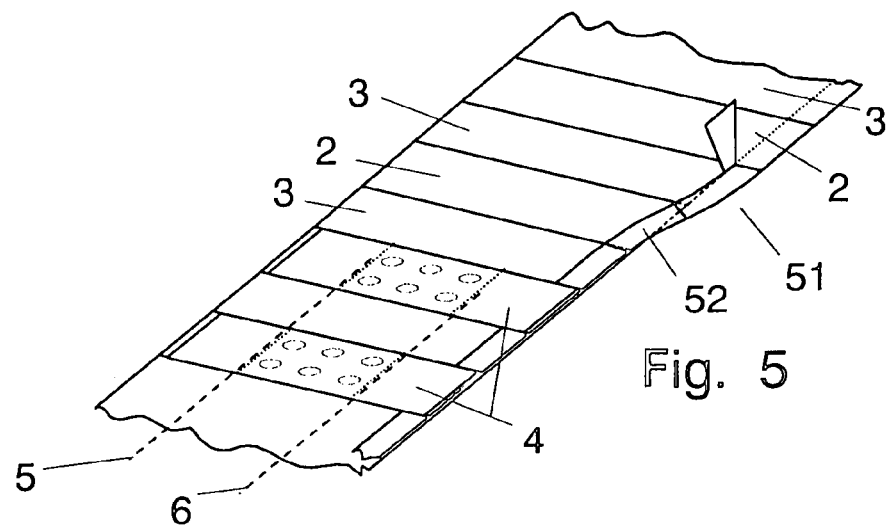
Figure 6:
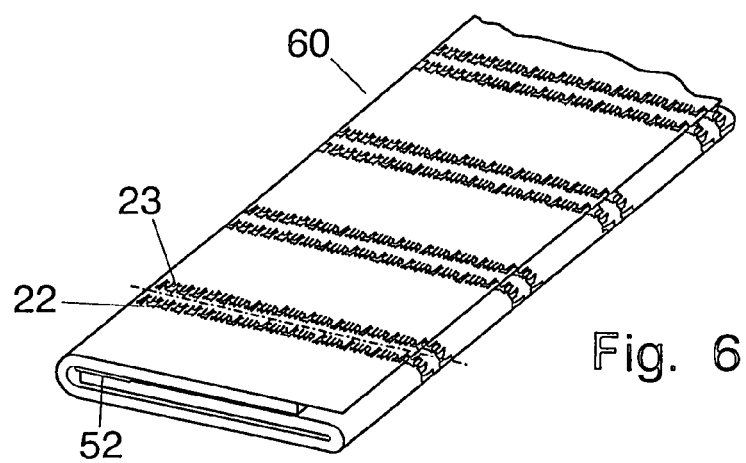
Figure 7:
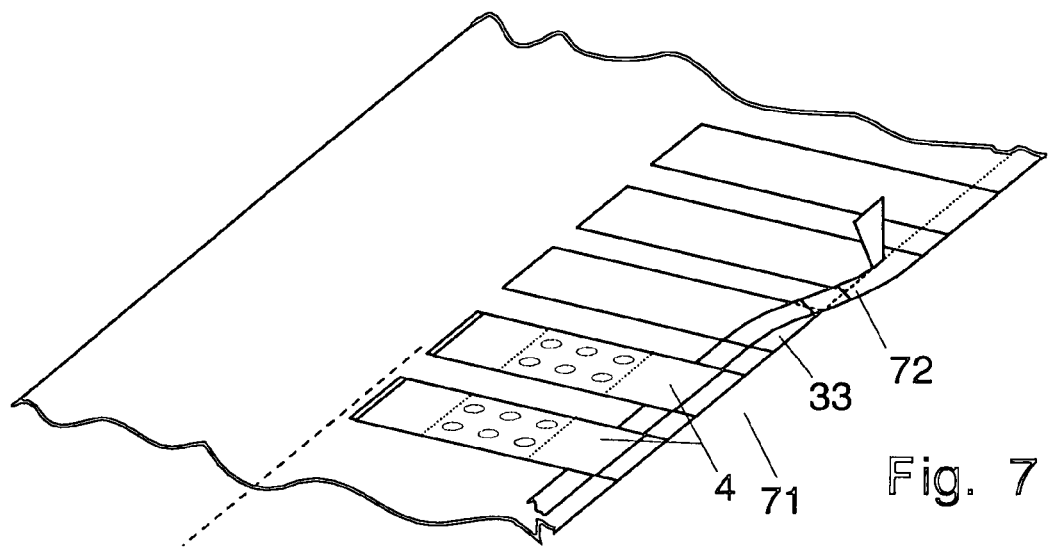
Figure 8:
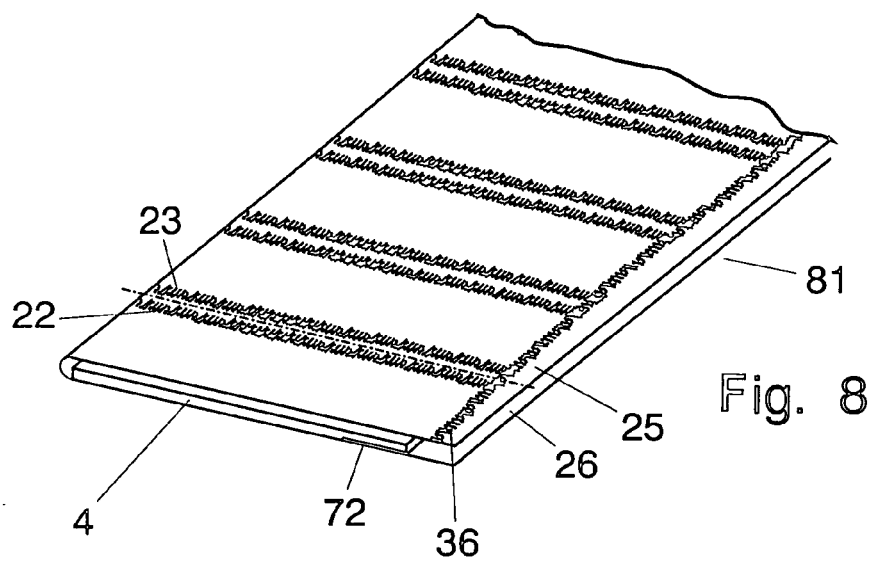
Figure 9:
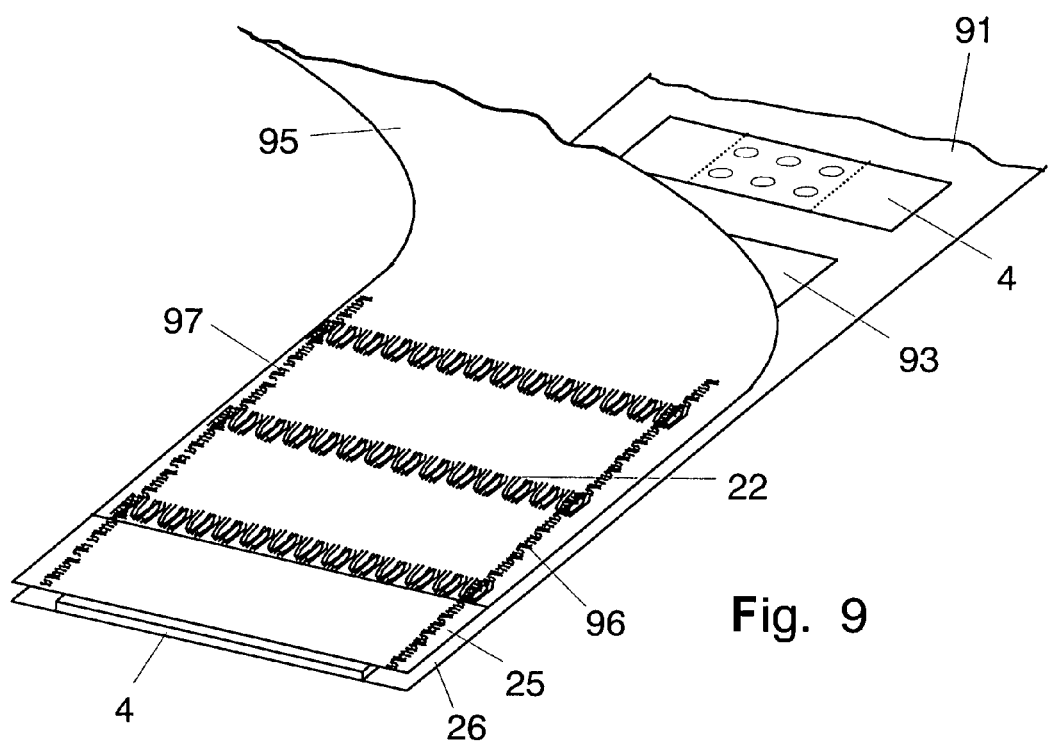
Figure 10:
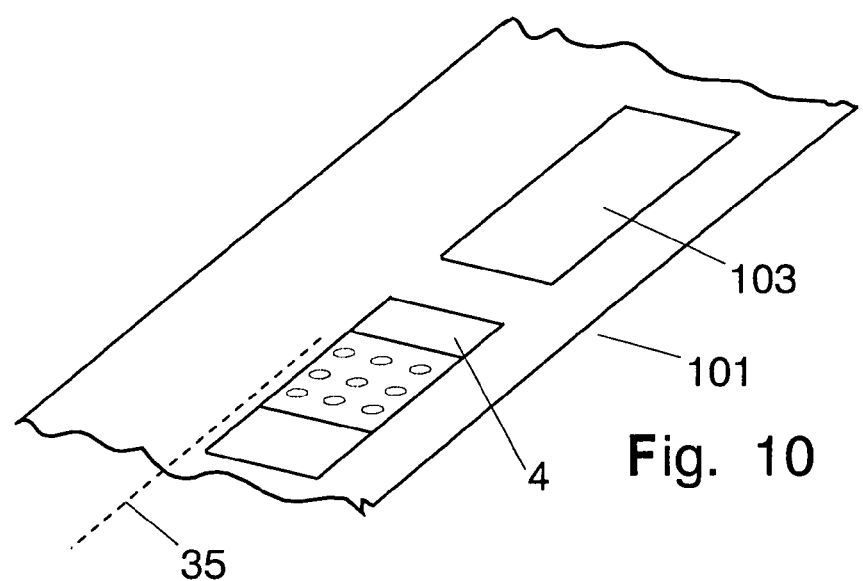
Figure 11:
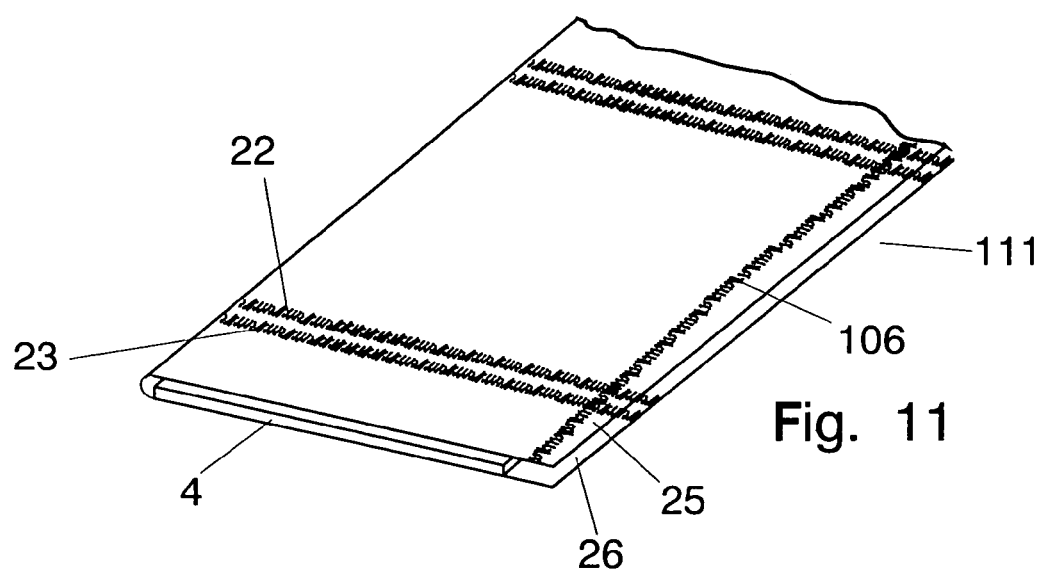
Figure 12:
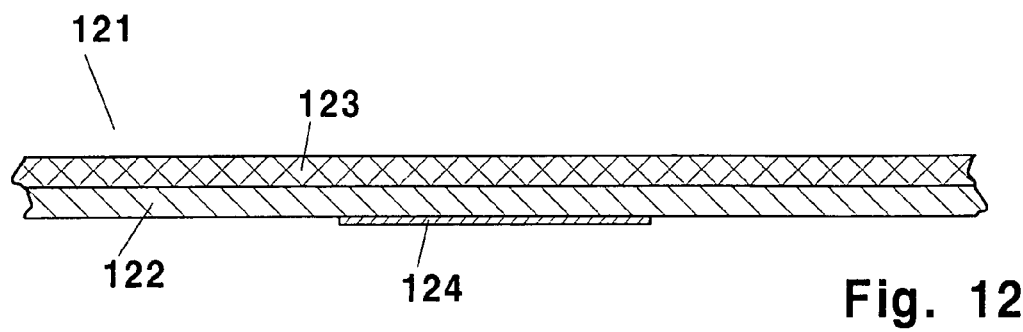
Figure 13:
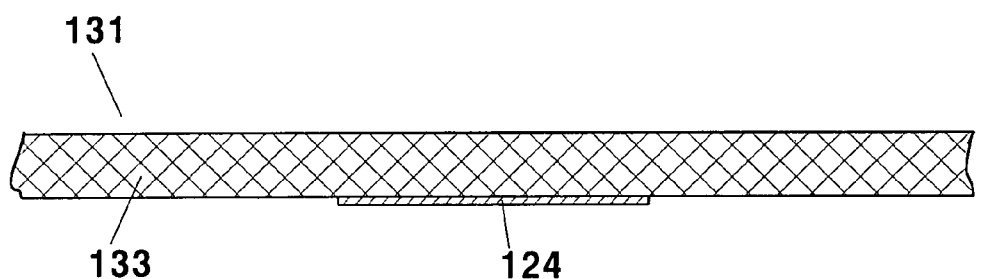
Figure 14:
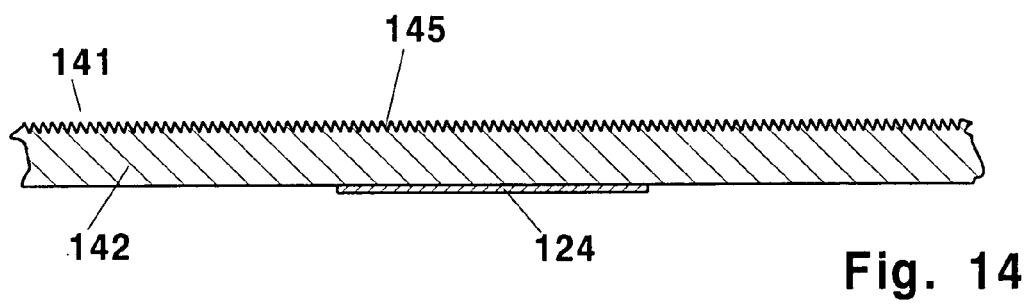
Figure 15:
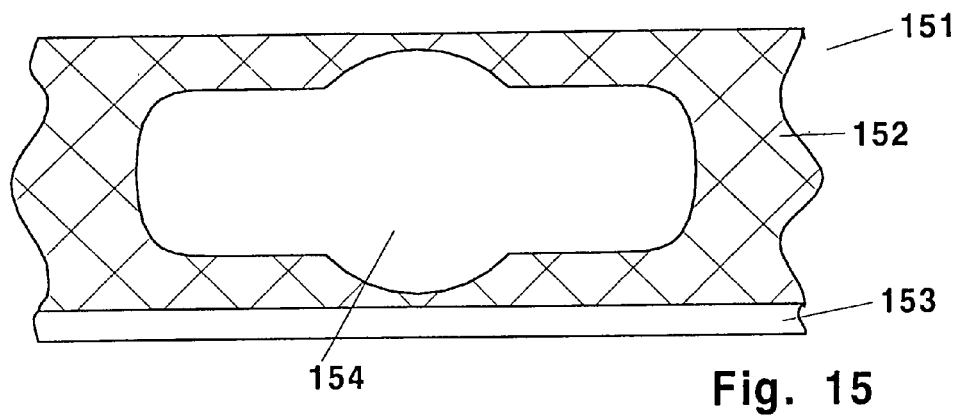
Figure 16:
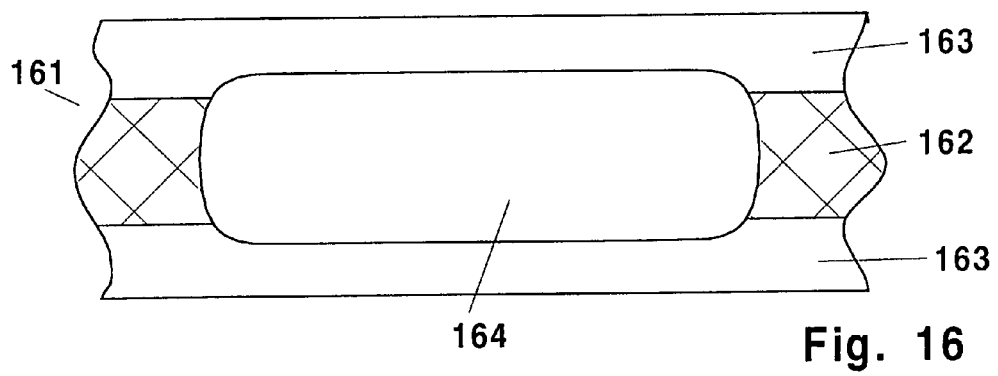
Figure 17:
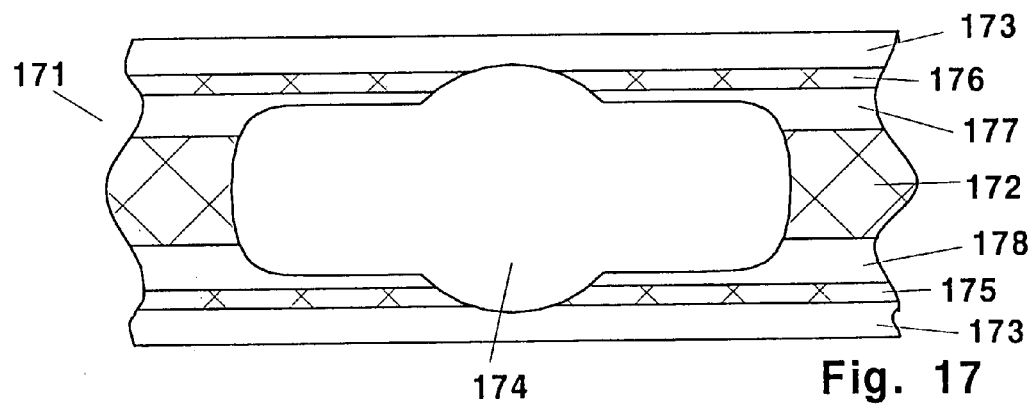
Figure 18:
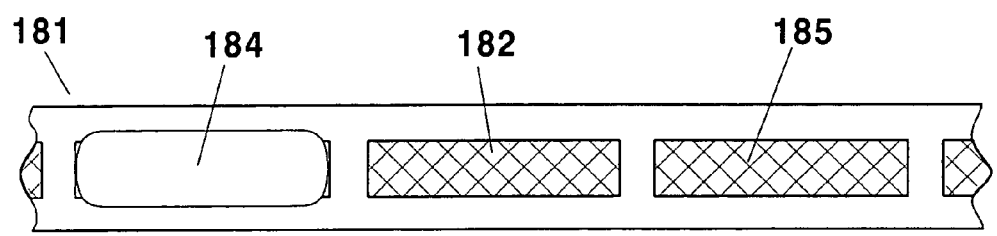
Figure 19:
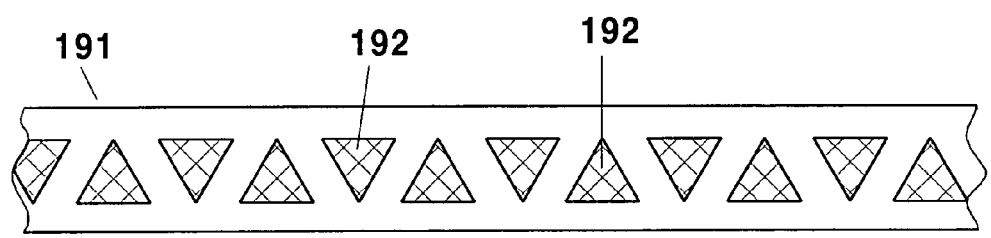

Several embodiments of the invention are illustrated in the drawings:

FIG. 1 shows a flat web of packaging material with transverse siliconized sections and sticking-plasters placed on them, FIG. 2 shows the web of packaging material illustrated in FIG. 1 after it has been folded together, FIG. 3 shows another web of packaging material provided with siliconized sections on which sticking-plasters have been placed, FIG. 4 shows the web of packaging material illustrated in FIG. 3 after it has been folded together along its longitudinal central axis, FIG. 5 shows another web of packaging material with transverse siliconized sections and sticking-plasters placed on them, FIG. 6 shows a web of packs folded along longitudinal folding lines out of the web of material illustrated in FIG. 5, FIG. 7 shows a partially siliconized web of material with a separated edge strip that is located beneath the plasters placed on the web, FIG. 8 shows a strip of packs produced from the web of packaging material illustrated in FIG. 7, FIG. 9 shows a web of packaging material with strip-like silicone sections, plasters placed on them and a further web of packaging material to cover the plasters, FIG. 10 shows a web of packaging material with longitudinal siliconized sections and plasters placed on them, FIG. 11 shows a web of packs produced by folding the web of material illustrated in FIG. 10, FIG. 12 is a vertical cross-section of a section of material, with a plastic film which is provided on one side with a nonwoven fabric and on the other side with a partial non-stick coating, FIG. 13 is a vertical cross-section of another section of material that is formed from a single-layer nonwoven fabric, which is provided with a partial non-stick coating on what will subsequently be the inside of the wrapper, FIG. 14 is a vertical cross-section of a section of material that consists of an embossed plastic film, FIG. 15 shows a section of a web of packaging material with a non-stick coating and an edge strip that does not have this coating and can be sealed, FIG. 16 shows a section of another web of packaging material with a central longitudinal strip that has a non-stick coating and with two edge strips that do not have a non-stick coating, FIG. 17 shows a section of another web of packaging material with three longitudinal strips that have a non-stick coating and that are each framed longitudinally by strips which do not have a non-stick coating, FIG. 18 shows a section of another web of packaging material with sections of non-stick coating located at longitudinal intervals and FIG. 19 shows a section of a web of packaging material with individual sections of a non-stick coating.

A web of packaging material 1 is shown in FIG. 1 that is provided with silicone-coated strips 2 extending at right angles to the longitudinal direction of the web across the entire width of the web, between which strips 3 without silicone coating are left.

Sticking-plasters 4 that are provided with self-adhesive sections which only stick to the silicone slightly and can therefore be detached from them again easily have been placed on the silicone-coated sections 2.5 and 6 are two folding lines, along which the two side sections of the web of packaging material 1 are folded onto the middle section of the same.

The result is then a strip of packs 21 as shown on a larger scale in FIG. 2. This strip of packs 21 has been cut off right next to a sticking-plaster 4 to show how the latter is wrapped. Two transverse crimped strips 22 and 23 with which individual packs for one plaster 4 each are divided off are located in the free space 3 between two sticking-plasters 4. A perforation line 24 is provided between these two crimped strips 22, 23 too, along which individual packs can be detached.

Individual packs can also simply be cut off instead of providing the perforation lines 24.

It is also possible to provide just one single crimped strip, within which the individual packs can then be separated.

An edge strip 25 of the web of packaging material 1 that is not covered by the sticking-plaster 4 is freely accessible and is easy to take hold of to open the individual pack. This edge strip 25 can also be stuck on, although it should be easy to remove.

In the embodiment shown in FIG. 3, a web of packaging material 30 is provided that only has siliconized strips 33 in one half to which sticking-plasters 4 are stuck with their self-adhesive sections. The web of packaging material 30 is folded together along a central folding line 35 to form a pack 40, as is shown in FIG. 4. The sticking-plaster 4 rests here on one side of the pack 40 and is covered by the other side.

Two crimped strips 22 and 23 which have the purpose of closing individual packs and between which these individual packs can be separated are provided in this embodiment too. The purpose of another longitudinal crimped seam 36 is to close the packs on all sides. This crimped seam 36 is located a certain distance away from the outside edge of the pack 40, as a result of which two flaps 25 and 26 are exposed that are easy to take hold of to open the individual packs. A glued seam can be provided instead of the crimped seam 36 too.

The embodiment shown in FIGS. 5 and 6 corresponds to a large extent to the embodiment illustrated in FIGS. 1 and 2; the only difference is that an edge strip 52 is separated off and placed beneath one end section of the sticking-plaster before the sticking-plasters 4 are placed on the siliconized strips 2 of the web of packaging material 51. The sticking-plasters 4 are particularly easy to remove from the web of packaging material as a result.

A pack 60 that has been folded together from the web of packaging material 51 is illustrated in FIG. 6. Crimped strips 22 and 23 which separate off individual packs and in the area of which the individual packs can be detached are provided here too.

In the embodiment shown in FIG. 7, the siliconized strips 33 again extend across only half the width of the web of packaging material 71, although they go all the way to the edge.

An edge strip 72 is cut off the web of packaging material 71 and is placed on the web of material in such a way that an adhesive section of the sticking-plaster rests on the edge strip before the sticking-plasters 4 are applied in this case too.

The web of packaging material 71 is then folded along its central longitudinal axis, as a result of which the sticking-plasters are covered completely.

Transverse and longitudinal crimped strips 22, 23 and 36 are again provided to separate off and close the individual packs, as is shown in FIG. 8 on the basis of the finished pack 81.

FIG. 9 shows an embodiment with a web of packaging material 91 that has been provided with transverse siliconized strips 93. The sticking-plasters 4 are placed on these siliconized strips 93. A further web of packaging material 95 is then placed on top and the two webs 91 and 95 are bonded together by means of two longitudinal crimped strips 96 and 97. Individual packs that can be detached by tearing them along a perforation line which is not shown in the drawing or by cutting them off are separated off by a transverse crimped strip 22. The purpose of the two free flaps 25 and 26 located outside one of the longitudinal crimped strips is to facilitate the opening of the individual pack.

FIG. 10 shows an embodiment of a web of packaging material 101 that has been provided with siliconized strips 103 which extend in the longitudinal direction of the web. Sticking-plasters 4 have then been placed on these strips 103 and have also been aligned in the longitudinal direction. The web of packaging material 101 is then folded together along the longitudinal central axis, as is illustrated in FIG. 11. The pack 111 that is produced as a result is divided up by transverse crimped strips 22 and 23 into individual packs which are in addition closed by a longitudinal crimped seam 106. The two flaps 25 and 26 are left outside this crimped seam 106 to open the individual packs.

121 in FIG. 12 is a section of material that is provided to produce a wrapper which is in turn designed to packaging sanitary towels. The section of material 121 consists of a plastic film 122, to one side of which a nonwoven fabric 123 has been applied. The plastic film is provided on the side facing away from the nonwoven fabric with a non-stick coating 124 that is only applied partially. When the section of material 121 is folded together, the non-stick coating 124 ends up on the inside and makes sure that the sanitary towel which is provided with one adhesive side only sticks slightly. As a result of the folding of the section of material 121, there are areas on the inside of the pack where at least two layers of the plastic film 122 rest directly on top of each other. The layers of the plastic film 122 are sealed or crimped together in these areas. The sealing or crimping operation is not impaired by the non-stick coating 124. The sanitary towel that only adheres slightly to the non-stick coating 124 is easy to remove from the pack.

The section of material 131 shown in FIG. 13 consists of a nonwoven fabric 133. This nonwoven fabric 133 is provided on part of one side with a non-stick coating 124. As is the case with the embodiment outlined above, the non-stick coating 124 ends up on the inside when the section of material is folded together. The adhesive side of a sanitary towel only sticks slightly to the non-stick coating 124. This guarantees that the sanitary towel is easy to remove from the pack. The sealability and crimpability of the layers of nonwoven fabric after they have been folded together are also guaranteed by the fact that the non-stick coating 124 is only partial.

The further embodiment that is illustrated in FIG. 14 shows a section of material 141. This section of material 141 consists of a plastic film 142 which is provided on one side with a textile-like embossing pattern 145. The film 142 is provided on part of the opposite side to the embossing pattern 145 with a non-stick coating 124. The non-stick coating 124 ends up on the inside when the section of material 141 is folded together. Due to the fact that the non-stick coating 124 has only been applied partially, the several layers of the section of material 141 that are formed in the folding process can be sealed or crimped together without any problems in the areas where the non-stick coating 124 has not been applied. Since its adhesive side only sticks slightly to the non-stick coating 124, the sanitary towel that is enclosed by the pack is easy to remove from the pack.

151 in FIG. 15 is another web of packaging material that is provided with a non-stick layer 152 as well as with an edge strip 153 which does not have a non-stick coating. As is shown in FIG. 15, an object 154 has been placed on the non-stick coating 152 that is to be wrapped in an appropriate section of the web of packaging material. The object 154—a sanitary towel with side wings in the embodiment illustrated—is provided on the underneath with a pressure sensitive adhesive that sticks to the non-stick coating 152 but is easy to detach again without losing its adhesive properties. Two side sections of the web of packaging material are folded over the sanitary towel to package it and the edge strips 153 resting on top of each other are sealed together. The opposite edge is then folded into position and the pack is closed in a way not illustrated in the drawing.

It is also possible to glue or crimp the edge strips instead of sealing them.

In the embodiment shown in FIG. 16, the web of packaging material 161 has a central longitudinal strip 162 with a non-stick coating that is enclosed by two edge strips 163. A sanitary towel without self-adhesive wings can again be placed on these non-stick longitudinal strips 162. If it is designed appropriately, this web of packaging material 161 can be used to package sticking-plasters 164 too.

In order to close a pack made from a section of this web of packaging material 161, the side sections are again folded into place to create a mutual overlap. A largely tight pack is then produced by bonding the two edge strips 163 together.

The purpose of the web of packaging material 171 shown in FIG. 17 is again to package a sanitary towel 174 with wings, in which the wings are provided with adhesive areas. The web of packaging material 171 is provided with three longitudinal strips 172, 175 and 176 with a release coating that are separated from each other by two longitudinal strips 177 and 178. These longitudinal strips 177 and 178 as well as the two edge strips 173 do not have a non-stick coating, so that at least the edge strips can be bonded together.

An embodiment of a web of packaging material 181 is illustrated in FIG. 18 in which the non-stick coatings 182, 185 are interrupted in the longitudinal direction and are only provided in the area where they are needed for the pressure sensitive adhesive of the object in question. The individual sections of the non-stick coating are located behind each other in the longitudinal direction. In this case it is possible to bond not only the edge strips but also the transverse sections without a release coating, so that a pack which is tight on all sides can be created.

FIG. 19, on the other hand, shows an embodiment of a web of packaging material 191 in which the sections of the non-stick coating 192 are only provided according to what is necessary in view of the product that is to be packaged.

Plastic films in the form of monofilms or multilayer films are possible materials for the web of packaging material. It is also feasible to use paper. Nonwoven fabrics can be chosen for the web of packaging material too. Not only the paper web but also the web of nonwoven fabric can be coated with plastic on at least one side.

Polysiloxanes have pro to be particularly successful non-stick coatings, while both solvent-based and solvent-free polysiloxanes can be used. The polysiloxanes are cured either thermally or by radiation.

The web of packaging material can in addition be provided with a print motif on the side opposite the release layer.

What is claimed is:

1. Web-like packaging material (1, 21, 31, 41, 51) in combination with an object for the wrapping on at least approximately all sides of said object (4, 24, 34) that is to be packaged and that is provided with an adhesive on at least sections of one side,
    wherein at least one section of the packaging material (1, 21, 31, 41, 51) which faces the adhesive is provided with non-stick sections, next to which sections are provided that do not have any non-stick material applied to them, and
    wherein at least one edge strip is provided on one end section of the packaging material and the at least one edge strip is disposed between the object and the packaging material.

2. Web-like packaging material combination according to claim 1,
    wherein at least one edge strip (3, 23, 33) of the web of packaging material (1, 21, 31, 41, 51) does not have any non-stick material applied to it.

3. Web-like packaging material combination according to claim 1,
    wherein an uninterrupted or interrupted longitudinal strip (22, 32, 42, 45) with a non-stick finish is provided in the middle of the web of packaging material (21, 31, 41), while at least the two longitudinal edges (23, 33) do not have a non-stick finish.

4. Web-like packaging material combination according to claim 1,
    wherein several longitudinal strips (32, 35, 36) with a non-stick finish and longitudinal strips (33, 37, 38) without a non-stick finish alternate parallel to each other.

5. Web-like packaging material combination according to claim 1,
    wherein individual sections with a non-stick finish (52) are provided that are located in accordance with the objects that are to be packaged and their adhesive coating.

6. Web-like packaging material combination according to claim 1,
    wherein the non-stick finish consists of polysiloxanes that are cured.

7. Web-like packaging material combination according to claim 1,
    wherein the web of packaging material (1, 21, 31, 41, 51) consists of a plastic film in the form of a monofilm or a multilayer film that can be embossed.

8. Web-like packaging material combination according to claim 1,
    wherein the web of packaging material (1, 21, 31, 41, 51) consists of paper.

9. Web-like packaging material combination according to claim 1,
    wherein the web of packaging material (1, 21, 31, 41, 51) consists of a nonwoven fabric.

10. Web-like packaging material combination according to claim 1,
    wherein a longitudinal section of the web of packaging material (1, 21, 31, 41, 51) is provided as a wrapper to package an object (4, 24, 34) that has an adhesive finish on one side.

11. Web-like packaging material combination according to claim 10,
    wherein the location of the non-stick finish (2, 22, 32, 35, 36, 42, 45) is chosen according to the object (4, 24, 34) that is to be packaged.

12. Web-like packaging material combination according to claim 1,
    wherein said object is a sanitary towel (4, 24, 34) which is provided with side wings, in the area of which the non-stick finish is provided.

13. Web-like packaging material combination according to claim 1,
    wherein the side of the web of packaging material facing away from the non-stick finish is provided with a print motif.

14. Web-like packaging material combination according to claim 8, wherein the paper is coated with plastic on at least one side.

15. Web-like packaging material combination according to claim 9,
    wherein the nonwoven fabric is provided with plastic on at least one side.

16. Web-like packaging material combination according to claim 1,
    wherein a section of the packaging material provided with the non-stick finish is used to cover the object.

17. Web-like packaging material combination according to claim 1,
    wherein the individual packs are closed and divided-off by crimping.

18. Web-like packaging material combination according to claim 1, wherein a covering section of the packaging material is folded along a longitudinal line towards another section of the packaging material.

19. Web-like packaging material combination according to claim 1,
    wherein between individual packs perforation lines are used to facilitate the detachment of individual packs.

20. Web-like packaging material combination according to claim 1,
    wherein an outer side, the side facing away from the non-stick finish, of the packaging material is equipped with a textile look.

21. Web-like packaging material combination according to claim 1,
    wherein an outside of the packaging material is embossed to give it a textile look.

22. Web-like packaging material combination according to claim 1,
    wherein the packaging material is embossed on an outside and is smooth on an inside.

23. Web-like packaging material combination according to claim 1,
    wherein the packaging material contains a nonwoven fabric as at least one layer.

24. Web-like packaging material combination according to claim 1,
    wherein said object is a panty-liner.

25. Web-like packaging material combination according to claim 1,
    wherein said object is a sanitary towel.

\* \* \* \* \*